(12) United States Patent
Zhou

(10) Patent No.: US 12,281,088 B2
(45) Date of Patent: Apr. 22, 2025

(54) PROCESS FOR THE SYNTHESIS OF VORTIOXETINE

(71) Applicant: Suzhou Fude Zhaofeng Biochemical Technology Co., Ltd, Suzhou (CN)

(72) Inventor: Lihua Zhou, Suzhou (CN)

(73) Assignee: SUZHOU FUDE ZHAOFENG BIOCHEMICAL TECHNOLOGY CO., LTD, Suzhou (CN)

( * ) Notice: Subject to any disclaimer, the term of this patent is extended or adjusted under 35 U.S.C. 154(b) by 819 days.

(21) Appl. No.: 17/435,262

(22) PCT Filed: Jan. 6, 2021

(86) PCT No.: PCT/CN2021/070481
§ 371 (c)(1),
(2) Date: Aug. 31, 2021

(87) PCT Pub. No.: WO2022/052391
PCT Pub. Date: Mar. 17, 2022

(65) Prior Publication Data
US 2022/0251055 A1 Aug. 11, 2022

(30) Foreign Application Priority Data

Sep. 10, 2020 (CN) .......................... 202010946679.9
Sep. 10, 2020 (CN) .......................... 202010946680.1

(51) Int. Cl.
*C07D 295/096* (2006.01)
*B01J 31/22* (2006.01)

(52) U.S. Cl.
CPC .......... *C07D 295/096* (2013.01); *B01J 31/22* (2013.01)

(58) Field of Classification Search
CPC ........................... C07D 295/096; B01J 31/22
See application file for complete search history.

(56) References Cited

U.S. PATENT DOCUMENTS 7,144,884 B2 12/2006 Ruhland et al.
8,476,279 B2 7/2013 Bang-Anderson

FOREIGN PATENT DOCUMENTS

| CN | 101472906 A | 7/2009 |
| CN | 103788020 A | 5/2014 |
| CN | 105339361 A | 2/2016 |
| WO | 2013/102573 A1 | 7/2013 |

OTHER PUBLICATIONS

Monkowius et al, Synthesis, Characterisation and Ligand Properties of Novel Bi-1,2,3-triazole ligands, Eur. J. Inorg. Chem, 2007, 4597-4606 (Year: 2007).*

* cited by examiner

*Primary Examiner* — Noble E Jarrell
*Assistant Examiner* — Phillip Matthew Rzeczycki
(74) *Attorney, Agent, or Firm* — HAUPTMAN HAM, LLP

(57) ABSTRACT

The present invention relates to a process for the synthesis of Vortioxetine (I) or a pharmaceutically acceptable salt thereof. This process is accomplished by using a catalytic system consisting of a copper salt and an organic ligand, which can promote the formation of both C—N and C—S bond in one-pot, giving rise to an efficient, simple and industrially viable synthetic route for Vortioxetine.

5 Claims, No Drawings

PROCESS FOR THE SYNTHESIS OF VORTIOXETINE

RELATED APPLICATIONS

The present application is a U.S. National Phase of International Application Number PCT/CN2021/070481 filed Jan. 6, 2021, and claims priority to Chinese Application Numbers CN 2020109466801, filed Sep. 10, 2020, and CN 2020109466799, filed Sep. 10, 2021.

FIELD OF THE INVENTION

The present invention relates to a process for the synthesis of Vortioxetine (I) or a pharmaceutically acceptable salt thereof.

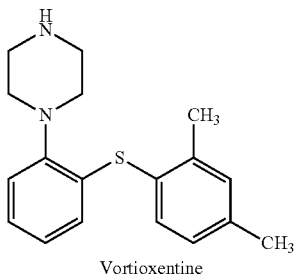

Vortioxentine

This process is accomplished by using a catalytic system consisting of a copper salt and an organic ligand, which can promote the formation of both C—N and C—S bond in one-pot, giving rise to an efficient, simple and industrially viable synthetic route for Vortioxetine.

BACKGROUND OF THE INVENTION

Vortioxetine, chemically known as 1-(2-((2,4-dimethylphenyl)thio)phenyl)piperazine, is represented by formula (1).

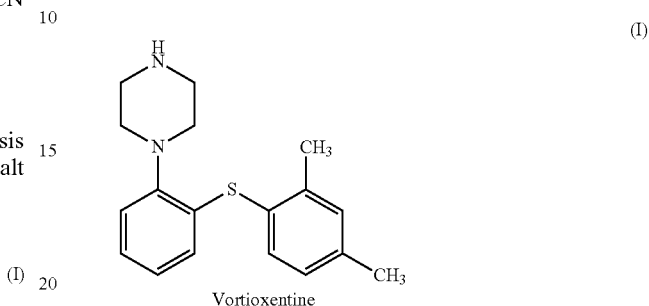

Vortioxentine

Vortioxetine and its acid addition salts thereof have affinity to the serotonin transporter and the serotonin receptors 3 and 1A (5-$HT_3$ and 5-$HT_{1a}$). The vortioxetine hydrobromide of empirical formula $C_{18}H_{22}N_2S$·HBr and CAS number of 960203-27-4 was approved by the USFDA and by EMA for the treatment of Major Depressive Disorder (MDD) as antidepressant drug and commercially sold under the brand name BRINTELLIX®.

The synthesis of Vortioxetine and its salt were described in U.S. Pat. Nos. 7,144,884, 8,476,279, WO2013102573, CN101472906, CN103788020 and CN105339361 Generally, they relied on palladium catalysts to form C—S and/or C—N bonds:

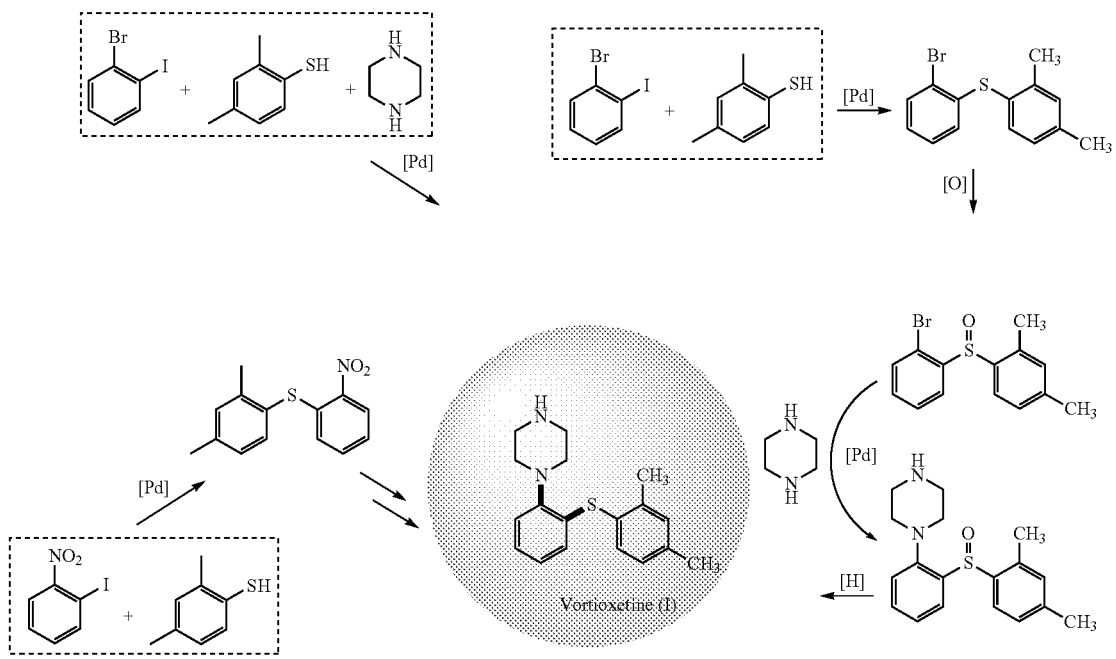

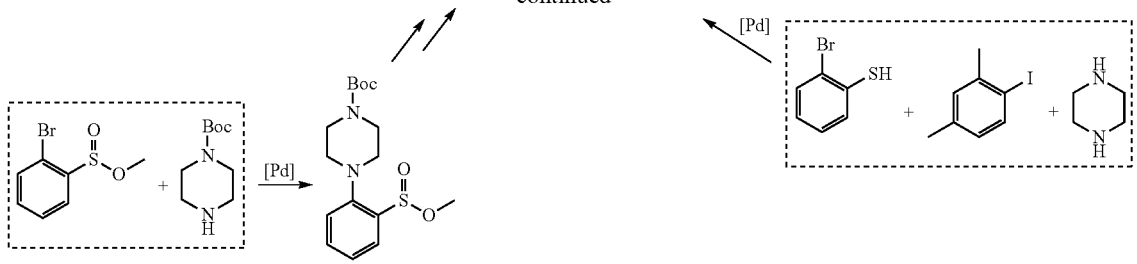

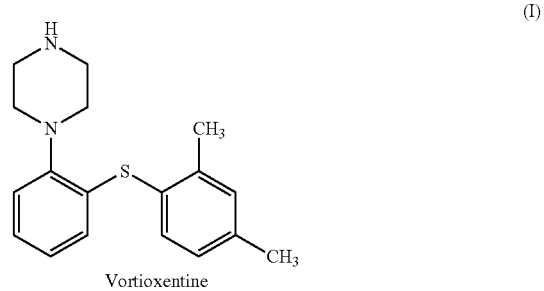 [SMILES: Cc1ccc(Sc2ccccc2N2CCNCC2)c(C)c1]

However, palladium is known to be very expensive, and its price is hundreds of times to non-noble metals such as copper, iron and nickel. The high cost of palladium catalysts has been limiting the use of such catalysts in industrial application including the manufacture of Vortioxetine.

Therefore, there still remains a need to improve such process and develop an efficient, cheap and industrially viable synthetic route, which can overcome the drawbacks of the prior art.

In order to overcome the problems associated with the prior art, it is herein described a new and improved process which provides Vortioxetine in higher yield using cheaper reagents.

Definitions

The following definitions are used in connection with the present application, unless it is indicated otherwise.

The term "room temperature" refers to a temperature ranging from about 15° C. to 35° C., preferably to a temperature ranging from about 20° C. to 30° C., more preferably to a temperature of 25° C.

The term "alkyl" refers to a straight or branched chain hydrocarbon containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

The term "aryl" refers to a monocyclic-ring system or a polycyclic-ring system wherein one or more of the fused rings are aromatic. Representative examples of aryl include, but are not limited to, anthracenyl, fluorenyl, indanyl, indenyl, naphthyl, and phenyl.

Abbreviations

| | |
|---|---|
| TEA | trimethylamine |
| DBU | 1,8-diazabicyclo[5.4.0]undec-7-ene |
| DIPEA | diisopropylethylamine |
| acac | acetylacetonyl |

SUMMARY OF THE INVENTION

In one aspect, a method for manufacturing Vortioxetine of Formula (I),

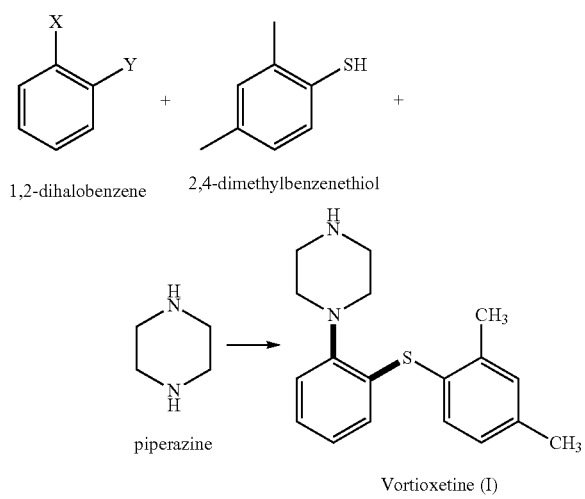

which comprises the reaction of 1,2-dihalobenzene, 2,4-dimethylbenzenethiol and piperazine in the presence of a base, a copper catalyst and a ligand, wherein X and Y are selected from the group consisting of —Cl, —Br, and —I.

The above process is a one-pot reaction with the same catalytic system (copper salt and ligand) promoting the formation of both C—S and C—N bonds in one reaction vessel.

DETAILED DESCRIPTION OF THE INVENTION

The present application is based on the discovery of a novel, alternative approach to synthesizing Vortioxetine. The synthesis described herein allows for the cost-effective preparation of Vortioxetine by reducing production time and cost.

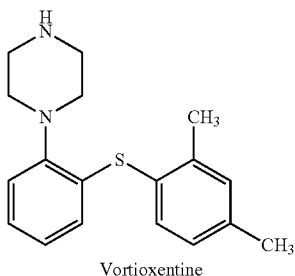

Vortioxentine

This approach provides a step-economical method for the low cost production of Vortioxetine. In order to realize a strategy based on cheap, readily available chemical inputs, step economy, and overall efficiency, novel copper catalytic system are relied on to promote the formation of both C—S and C—N bonds in one-pot reaction.

In one aspect, a synthetic method is provided as outlined below:

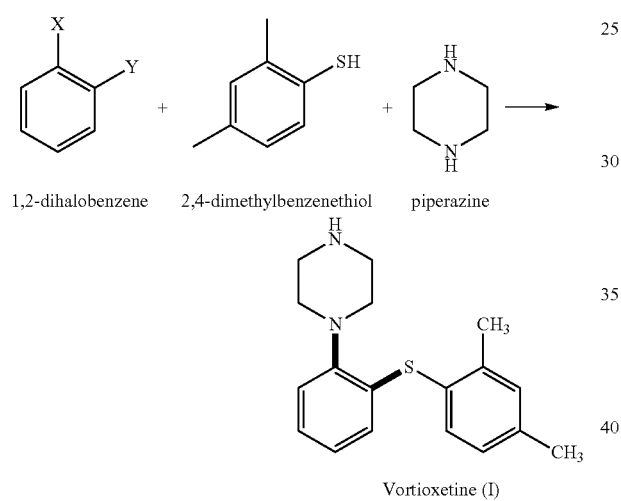

Vortioxetine (I)

The synthesis is accomplished by the coupling of 1,2-dihalobenzene, 2,4-dimethylbenzenethiol and piperazine in the presence of a base, a copper catalyst and a ligand to form Vortioxetine in one-pot reaction.

For the structure of 1,2-dihalobenzene, X and Y are selected from the group consisting of —Cl, —Br, and —I.

The base herein is selected from any organic and inorganic base such as TEA, DBU, DIPEA, KOH, $K_2CO_3$, NaOH, $Na_2CO_3$, $Cs_2CO_3$, CsOH, $K_3PO_4$, $K_2HPO_4$, $Na_3PO_4$, and $Na_2HPO_4$. Example copper catalysts include CuI, CuCl, CuBr, $Cu_2O$, $Cu(acac)_2$, $CuCl_2$, $CuBr_2$, CuI$_t$, $Cu(OAc)_2$, $Cu(OTf)_2$, $Cu(ClO_4)_2$, and $CuSO_4$. The ligand is selected from compound of formula (II),

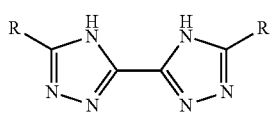

Wherein R is selected from any alkyl and substituted/unsubstituted aryl groups. Preferably, R is selected from methyl, ethyl, propyl, isopropyl, tertbutyl; and substituted/unsubstituted anthracenyl, fluorenyl, indanyl, indenyl, naphthyl, and phenyl groups. Some examples of formula VII are listed as following (L1-L10):

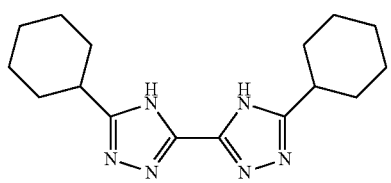

L1

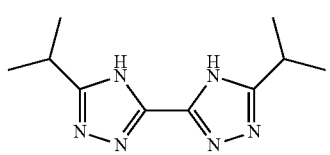

L2

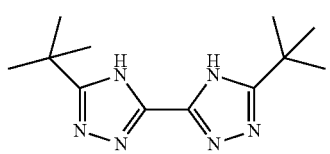

L3

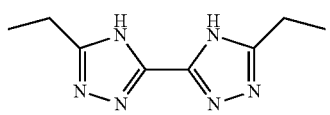

L4

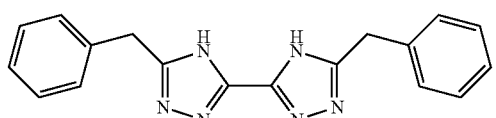

L5

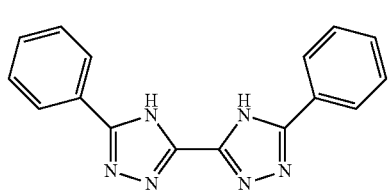

L6

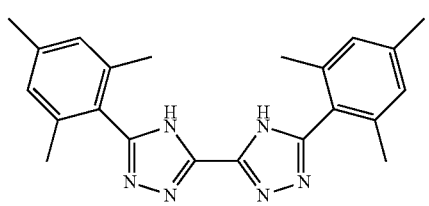

L7

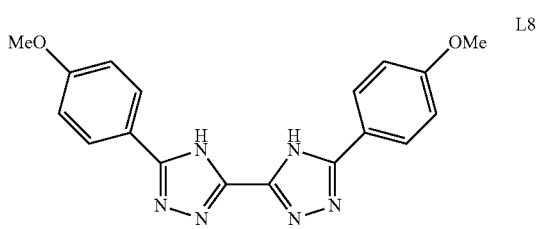

L8

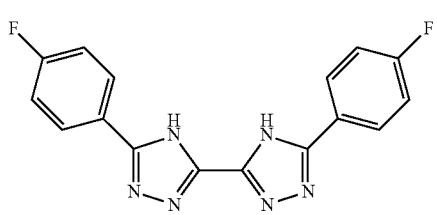

L9

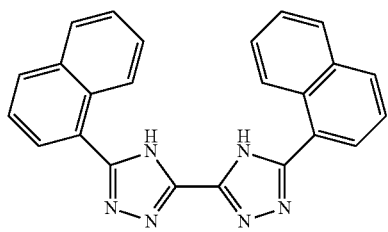

L10

The compound of formula (II) can be prepared by the reaction of an aldehyde, oxalohydrazide and ammonia acetate as showed in following scheme:

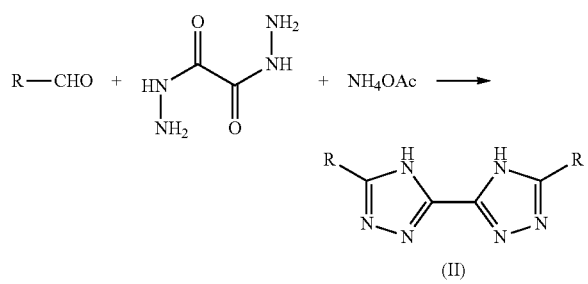

(II)

EXAMPLE

Detailed experimental parameters suitable for the preparation of Vortioxetine according to the present invention are provided by the following examples, which are intended to be illustrative and not limiting.

Unless otherwise noted, all materials, solvents and reagents, including anhydrous solvents such as DMF and DCM, were obtained from commercial suppliers, of the best grade, and used without further purification. All reactions involving air- or moisture-sensitive compounds were performed under nitrogen or argon atmosphere, unless otherwise noted.

The $^1$H (400 MHz) and $^{13}$C NMR (100 MHz) data were recorded on Bruker AVANCE II 400 MHz spectrometer using CDCl$_3$ or DMSO-D$_6$ as solvent. The chemical shifts ($\delta$) are reported in ppm and coupling constants (J) in Hz. $^1$H NMR spectra was recorded with tetramethylsilane ($\delta$=0.00 ppm) as internal reference; $^{13}$C NMR spectra was recorded with CDCl$_3$ ($\delta$=77.00 ppm) or DMSO-D$_6$ ($\delta$=39.5 ppm) as internal reference.

The synthesis of L1:

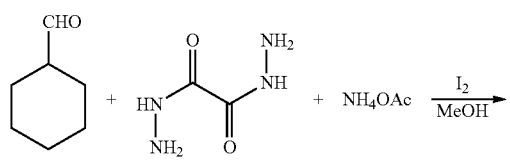

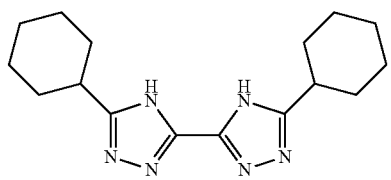

L1

To a solution of cyclohexanecarbaldehyde (11.2 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 20 h before being filtered. The resulted solid was washed with methanol (50 mL) three times and ether (50 mL), then dried under vacuum to afford desired L1 as yellow solid. Yield: 12 g, 80%. $^1$H NMR (400 MHz, CDCl$_3$) $\delta$ 11.12 (brs, 2H), 2.69-2.75 (m, 2H), 1.61-1.86 (m, 8H), 1.33-1.63 (m, 12H). $^{13}$C NMR (100 MHz, CDCl$_3$) $\delta$ 163.5, 159.3, 39.5, 33.0, 26.1, 26.4. ESI-TOF-HRMS calculated for C$_{16}$H$_{24}$N$_6$Na (M+Na) 323.1960, found 323.1924.

The synthesis of L5:

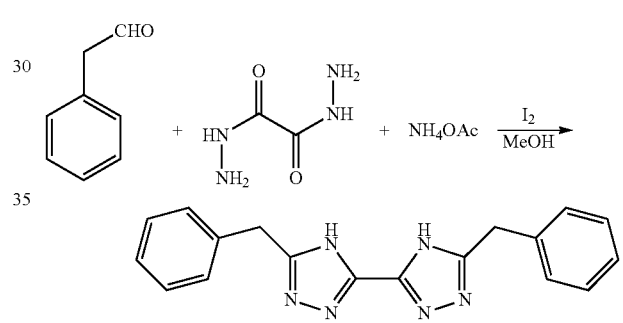

L5

To a solution of 2-phenylacetaldehyde (12 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 17 h before being filtered. The resulted solid was washed with methanol (50 mL) three times and ether (50 mL), then dried under vacuum to afford desired L5 as yellow solid. Yield: 12 g, 76%. $^1$H NMR (400 MHz, CDCl$_3$) $\delta$ 11.12 (brs, 2H), 7.26-7.30 (m, 4H), 7.18-7.25 (m, 6H), 4.02 (s, 4H). $^{13}$C NMR (100 MHz, CDCl$_3$) $\delta$ 163.5, 159.6, 136.5, 129.1, 128.6, 125.5, 34.2. ESI-TOF-HRMS calculated for C$_{18}$H$_{16}$N$_6$Na (M+Na) 339.1329, found 339.1313.

The synthesis of L6:

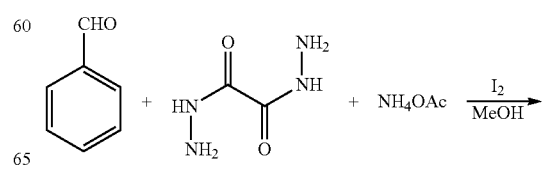

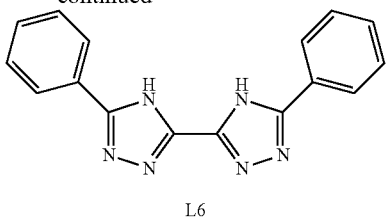

L6

To a solution of benzaldehyde (10.6 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 18 h before being filtered. The resulted solid was washed with methanol (50 mL) three times and ether (50 mL), then dried under vacuum to afford desired L6 as yellow solid. Yield: 11 g, 77%. $^1$H NMR (400 MHz, CDCl$_3$) δ 11.12 (brs, 2H), 8.05-8.09 (m, 4H), 7.43-7.51 (m, 6H). $^{13}$C NMR (100 MHz, CDCl$_3$) δ 163.5, 157.6, 132.5, 131.1, 129.2, 127.5. ESI-TOF-HRMS calculated for C$_{16}$H$_{12}$N$_6$Na (M+Na) 311.1021, found 311.1003.

The synthesis of L7:

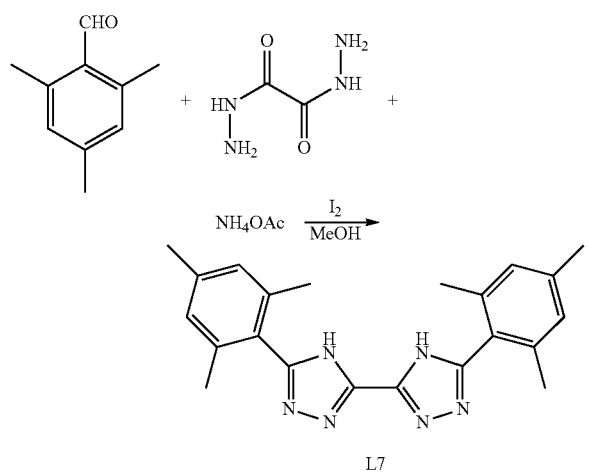

L7

To a solution of benzaldehyde (14.8 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 24 h before being filtered. The resulted solid was washed with methanol (50 mL) three times and ether (50 mL), then dried under vacuum to afford desired L7 as yellow solid. Yield: 12 g, 65%. $^1$H NMR (400 MHz, CDCl$_3$) δ 11.12 (brs, 2H), 7.01 (s, 4H), 2.57 (s, 12H), 2.48 (s, 6H). $^{13}$C NMR (100 MHz, CDCl$_3$) δ 163.5, 157.6, 138.2, 136.1, 128.2, 122.5, 21.9, 19.3. ESI-TOF-HRMS calculated for C$_{22}$H$_{24}$N$_6$Na (M+Na) 395.1960, found 395.1932.

The synthesis of Vortioxetine and its salt with 1,2-diiodobenzene and L1:

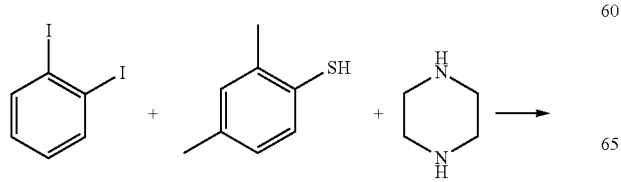

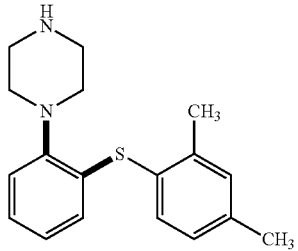

Vortioxetine (I)

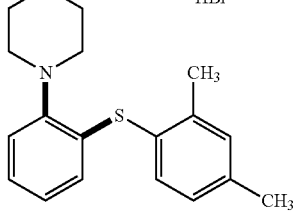

Vortioxetine·HBr

To a solution of 1,2-diiodobenzene (33.0 g, 100 mmol), 2,4-dimethylbenzenethiol (15.2 g, 110 mmol), piperazine (9.5 g, 110 mmol) and K$_3$PO$_4$ (23.3 g, 110 mmol) in DMF (100 mL), was added CuI (1.9 g, 10 mmol) and L1 (3 g, 10 mmol). The reaction mixture was stirred at 100° C. for 10 h before being partitioned between ethyl acetate (300 mL) and water (100 mL). The combined organics were dried over MgSO$_4$, filtered and concentrated in vacuum to give a crude product of Vortioxetine, which was purified by being converted to Vortioxetine hydrobromide (Vortioxetine·HBr). The crude product of Vortioxetine was dissolved in acetone (150 mL), then aqueous hydrobromic acid was added at room temperature, the pH of the solution was adjusted to 1-3, leading to the precipitation of white solid which was filtered and washed with acetone (30 mL), dried under vacuum to afford Vortioxetine·HBr as white solid. Yield: 28 g, 74%.

The synthesis of Vortioxetine and its salt with 1,2-dibromobenzene and L5:

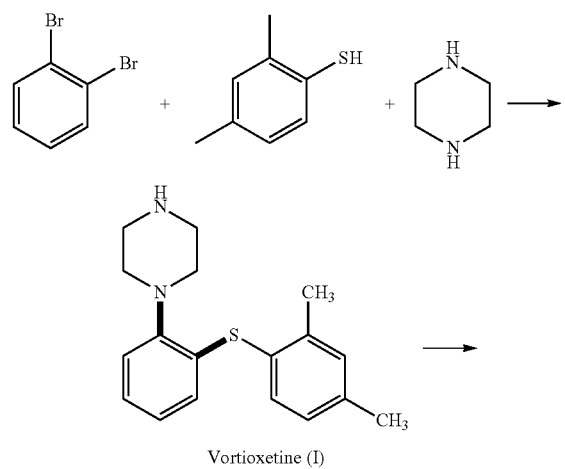

Vortioxetine (I)

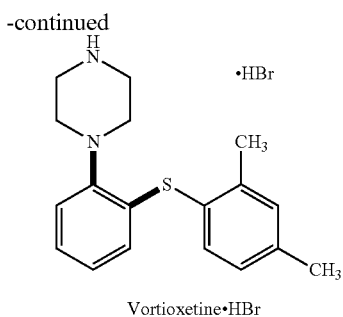

Vortioxetine•HBr

To a solution of 1,2-dibromobenzene (23.3 g, 100 mmol), 2,4-dimethylbenzenethiol (15.2 g, 110 mmol), piperazine (9.5 g, 110 mmol) and K₃PO₄ (23.3 g, 110 mmol) in DMF (100 mL), was added CuI (1.9 g, 10 mmol) and L5 (3.1 g, 10 mmol). The reaction mixture was stirred at 110° C. for 11 h before being partitioned between ethyl acetate (300 mL) and water (100 mL). The combined organics were dried over MgSO₄, filtered and concentrated in vacuum to give a crude product of Vortioxetine, which was purified by being converted to Vortioxetine hydrobromide (Vortioxetine•HBr). The crude product of Vortioxetine was dissolved in acetone (150 mL), then aqueous hydrobromic acid was added at room temperature, the pH of the solution was adjusted to 1-3, leading to the precipitation of white solid which was filtered and washed with acetone (30 mL), dried under vacuum to afford Vortioxetine•HBr as white solid. Yield: 27 g, 71%.

The synthesis of Vortioxetine and its salt with 1,2-dichlorobenzene and L6:

To a solution of 1,2-dichlorobenzene (14.6 g, 100 mmol), 2,4-dimethylbenzenethiol (15.2 g, 110 mmol), piperazine (9.5 g, 110 mmol) and K₂CO₃ (15.2 g, 110 mmol) in DMSO (100 mL), was added Cu(OTf)₂ (3.6 g, 10 mmol) and L6 (2.9 g, 10 mmol). The reaction mixture was stirred at 120° C. for 12 h before being partitioned between ethyl acetate (300 mL) and water (100 mL). The combined organics were dried over MgSO₄, filtered and concentrated in vacuum to give a crude product of Vortioxetine, which was purified by being converted to Vortioxetine hydrobromide (Vortioxetine•HBr). The crude product of Vortioxetine was dissolved in acetone (150 mL), then aqueous hydrobromic acid was added at room temperature, the pH of the solution was adjusted to 1-3, leading to the precipitation of white solid which was filtered and washed with acetone (30 mL), dried under vacuum to afford Vortioxetine•HBr as white solid. Yield: 29 g, 77%.

The synthesis of Vortioxetine and its salt with 1-bromo-2-chlorobenzene and L6:

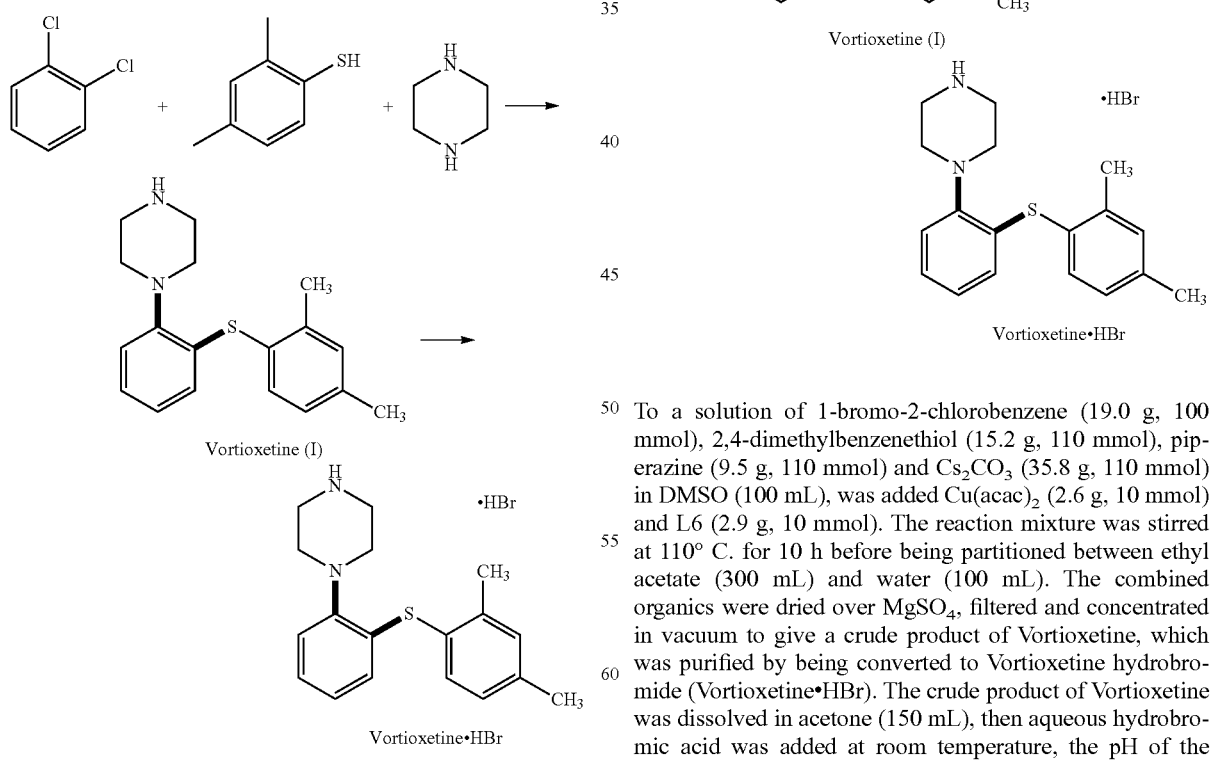

To a solution of 1-bromo-2-chlorobenzene (19.0 g, 100 mmol), 2,4-dimethylbenzenethiol (15.2 g, 110 mmol), piperazine (9.5 g, 110 mmol) and Cs₂CO₃ (35.8 g, 110 mmol) in DMSO (100 mL), was added Cu(acac)₂ (2.6 g, 10 mmol) and L6 (2.9 g, 10 mmol). The reaction mixture was stirred at 110° C. for 10 h before being partitioned between ethyl acetate (300 mL) and water (100 mL). The combined organics were dried over MgSO₄, filtered and concentrated in vacuum to give a crude product of Vortioxetine, which was purified by being converted to Vortioxetine hydrobromide (Vortioxetine•HBr). The crude product of Vortioxetine was dissolved in acetone (150 mL), then aqueous hydrobromic acid was added at room temperature, the pH of the solution was adjusted to 1-3, leading to the precipitation of white solid which was filtered and washed with acetone (30 mL), dried under vacuum to afford Vortioxetine•HBr as white solid. Yield: 28 g, 74%.

The synthesis of Vortioxetine and its salt with 1-chloro-2-iodobenzene and L7:

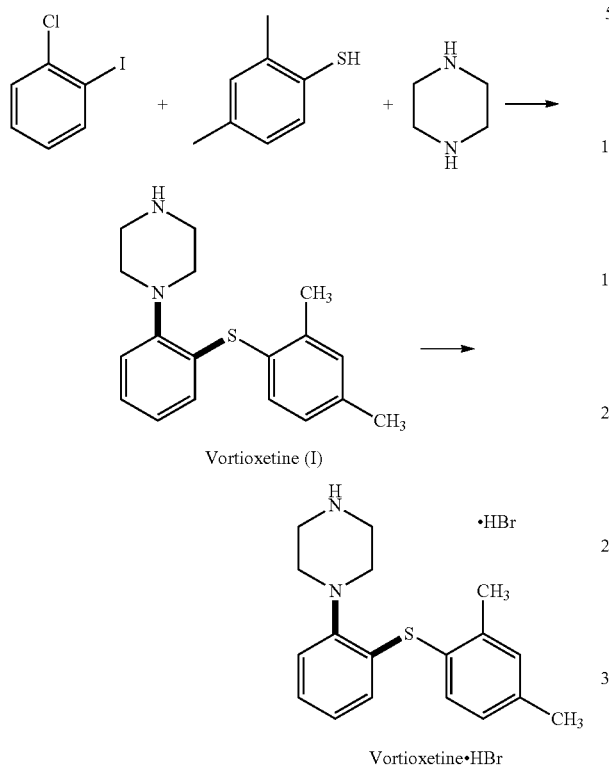

Vortioxetine (I)

Vortioxetine•HBr

To a solution of 1-chloro-2-iodobenzene (23.8 g, 100 mmol), 2,4-dimethylbenzenethiol (15.2 g, 110 mmol), piperazine (9.5 g, 110 mmol) and K$_2$CO$_3$ (15.2 g, 110 mmol) in CH$_3$CN (100 mL), was added CuCl (1.0 g, 10 mmol) and L7 (3.7 g, 10 mmol). The reaction mixture was stirred at 110° C. for 10 h before being partitioned between ethyl acetate (300 mL) and water (100 mL). The combined organics were dried over MgSO$_4$, filtered and concentrated in vacuum to give a crude product of Vortioxetine, which was purified by being converted to Vortioxetine hydrobromide (Vortioxetine•HBr). The crude product of Vortioxetine was dissolved in acetone (150 mL), then aqueous hydrobromic acid was added at room temperature, the pH of the solution was adjusted to 1-3, leading to the precipitation of white solid which was filtered and washed with acetone (30 mL), dried under vacuum to afford Vortioxetine•HBr as white solid. Yield: 26.5 g, 70%.

The synthesis of Vortioxetine and its salt with 1-bromo-2-iodobenzene and L5:

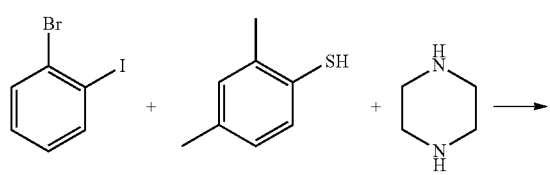

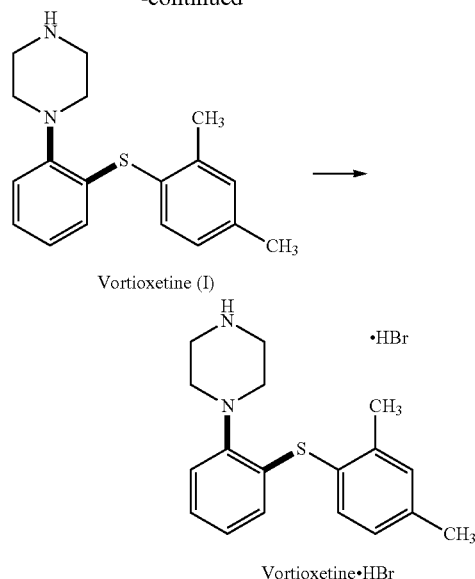

Vortioxetine (I)

Vortioxetine•HBr

To a solution of 1-bromo-2-iodobenzene (28.2 g, 100 mmol), 2,4-dimethylbenzenethiol (15.2 g, 110 mmol), piperazine (9.5 g, 110 mmol) and K$_2$CO$_3$ (15.2 g, 110 mmol) in DMF (100 mL), was added CuCl (1.0 g, 10 mmol) and L5 (3.1 g, 10 mmol). The reaction mixture was stirred at 100° C. for 9 h before being partitioned between ethyl acetate (300 mL) and water (100 mL). The combined organics were dried over MgSO$_4$, filtered and concentrated in vacuum to give a crude product of Vortioxetine, which was purified by being converted to Vortioxetine hydrobromide (Vortioxetine•HBr). The crude product of Vortioxetine was dissolved in acetone (150 mL), then aqueous hydrobromic acid was added at room temperature, the pH of the solution was adjusted to 1-3, leading to the precipitation of white solid which was filtered and washed with acetone (30 mL), dried under vacuum to afford Vortioxetine•HBr as white solid. Yield: 29 g, 77%.

Vortioxetine•HBr obtained from above examples has the following characteristics:

$^1$H NMR (d$_6$-DMSO, 400 MHz): 7.40 (m, 1H), 7.14 (m, 3H), 7.06 (m, 1H), 6.87 (m, 2H), 3.13 (br, 8H), 2.41 (s, 3H), 2.38 (s, 3H). ESI-TOF-HRMS calculated for C$_{18}$H$_{23}$N$_2$S$^+$ (Vortioxetine+H$^+$) 299.1576, found 299.1543.

The invention claimed is:

1. A catalyst system, which comprises a copper catalyst and a ligand, and the ligand is formula (L1)

2. The catalyst system of claim 1, wherein the copper catalyst is selected from CuI, CuCl, CuBr, Cu$_2$O, Cu(acac)$_2$ CuCl$_2$, CuBr$_2$, CuI$_2$, Cu(OAc)$_2$, Cu(OTf)$_2$, Cu (ClO$_4$)$_2$, and CuSO$_4$.

3. A method for manufacturing Vortioxetine (I),

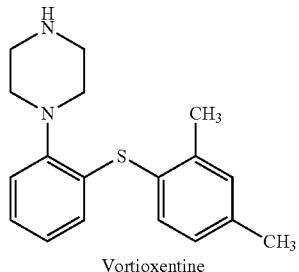
Vortioxentine (I)

which comprises the reaction of 1,2-dihalobenzene, 2,4-dimethylbenzenethiol and piperazine in the presence of a base and the catalyst system according to claim 1

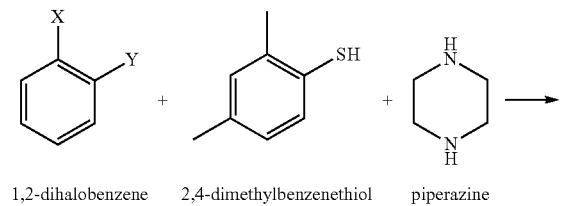

1,2-dihalobenzene    2,4-dimethylbenzenethiol    piperazine

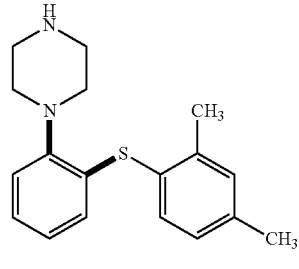
Vortioxetine (I)

wherein X and Y are selected from the group consisting of —Cl, —Br, and —I.

4. The method of claim 3, wherein the base is selected from TEA, DBU, DIPEA, KOH, $K_2CO_3$, NaOH, $Na_2CO_3$, $Cs_2CO_3$, CsOH, $K_3PO_4$, $K_2HPO_4$, $Na_3PO_4$, and $Na_2HPO_4$.

5. The method of claim 3, wherein all the reactions are carried out in one-pot.

* * * * *